United States Patent
Alfano (10) Patent No.: US 9,561,077 B2
(45) Date of Patent: *Feb. 7, 2017

(54) METHOD OF USING SUPERCONTINUUM LIGHT FOR MEDICAL AND BIOLOGICAL APPLICATIONS

(71) Applicant: Robert R. Alfano, Bronx, NY (US)

(72) Inventor: Robert R. Alfano, Bronx, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/996,449

(22) Filed: Jan. 15, 2016

(65) Prior Publication Data

US 2016/0128775 A1     May 12, 2016

Related U.S. Application Data

(62) Division of application No. 12/723,091, filed on Mar. 12, 2010, now Pat. No. 9,414,887.

(60) Provisional application No. 61/209,969, filed on Mar. 13, 2009.

(51) Int. Cl.

| | | |
|---|---|---|
| *A61B 18/20* | (2006.01) | |
| *A61B 5/00* | (2006.01) | |
| *A61B 17/00* | (2006.01) | |
| *G02F 1/355* | (2006.01) | |
| *G02F 1/35* | (2006.01) | |
| *A61B 18/18* | (2006.01) | |

(52) U.S. Cl.
CPC .............. *A61B 18/20* (2013.01); *A61B 5/0066* (2013.01); *A61B 2017/00508* (2013.01); *A61B 2018/1807* (2013.01); *A61B 2018/2065* (2013.01); *G02F 1/355* (2013.01); *G02F 2001/3528* (2013.01)

(58) Field of Classification Search
CPC . G03F 7/202; G02B 21/0044; G02B 21/0048; A61B 1/00; A61B 2018/1807; A61B 2018/2065; A01B 12/006; G02F 2001/3528
USPC ............ 372/21, 101, 25; 385/122; 356/318; 128/898; 606/2, 5–19, 88–94; 600/407, 600/478; 216/48
See application file for complete search history.

(56) References Cited

U.S. PATENT DOCUMENTS

| | | | |
|---|---|---|---|
| 4,288,528 A | 9/1981 | Picquendar et al. | |
| 5,532,873 A | 7/1996 | Dixon | |
| 6,450,949 B1 | 9/2002 | Farkas et al. | |
| 6,641,599 B2* | 11/2003 | Peterson | A61H 39/00 |
| | | | 128/898 |
| 6,700,905 B1* | 3/2004 | Karasawa | G02F 1/353 |
| | | | 372/21 |
| 6,826,209 B1* | 11/2004 | Morita | H01S 3/0057 |
| | | | 372/101 |

(Continued)

OTHER PUBLICATIONS

Y.-H. Chen Single-shot, space- and time-resolved measurement Sep. 3, 2007 / vol. 15, No. 18 / Optics Express 11341.*

(Continued)

*Primary Examiner* — Gary Jackson
*Assistant Examiner* — Victor Shapiro
(74) *Attorney, Agent, or Firm* — Myron Greenspan Lackenbach Siegel LLP (57) ABSTRACT

A method and an apparatus are provided for producing SuperContinuum (SC) light for medical and biological applications is provided. Pulses are focused from a laser system into at least one of a pressurized cell and one or more fibers. A pump pulse is converted into the SC light at a specified rate of repetition. The SC light is applied at the specified rate of repetition to tissue for medical and biological applications.

25 Claims, 4 Drawing Sheets

(56) References Cited

U.S. PATENT DOCUMENTS

| | | | |
|---|---|---|---|
| 2004/0233944 A1* | 11/2004 | Dantus | G01N 21/4795 |
| | | | 372/25 |
| 2006/0198588 A1* | 9/2006 | Kuksenkov | G02B 6/02242 |
| | | | 385/122 |
| 2006/0291042 A1 | 12/2006 | Alfano et al. | |
| 2007/0162093 A1* | 7/2007 | Porter | A61N 5/0613 |
| | | | 607/89 |
| 2008/0030727 A1* | 2/2008 | Chin | G01N 21/6402 |
| | | | 356/318 |

OTHER PUBLICATIONS

R. R. Alfano et al., PRL, 24, 592-594, 584-587, 1219-1222, (1970).
See, K. J. Ranha et al., Opt. Lett. 25, 25 (2000), and S. Coen, Chau, Leonhardt, and J. Harvey, JOSA B, 26, 753 (2002).
P. B. Corkum et al., PRL, 57, 2268 (1986).
Lehmeier et al., Opt. Comm., 56, 67-72 (1985).

* cited by examiner

METHOD OF USING SUPERCONTINUUM LIGHT FOR MEDICAL AND BIOLOGICAL APPLICATIONS

BACKGROUND OF THE INVENTION

1. Field of the Invention

The present invention relates generally to SuperContinuum (SC) light, and more particularly, to methods and apparatus for producing the SC light for medical and biological applications.

2. Description of the Related Art

Light is one of nature's most important and versatile phenomena. In a manner similar to that of a courier, light can transfer information from one point to another, and in a manner similar to that of an alchemist, it can alter matter and stimulate chemical reactions. More specifically, light can initiate and moderate key processes in chemistry, biology and condensed matter.

The versatility of light is a direct result of the many forms it is able to take, such as, for example, brief flashes, focused spots, broad continuous beams, dim or intense light, polarized light, low- or high-frequency light, and light containing many frequencies at once. The frequency of visible light determines its color, and is related to the light's wavelength, i.e., shorter wavelengths correspond to higher frequencies.

An incandescent bulb emits light across a full visible spectrum, resulting in white light. However, light from an incandescent bulb has several drawbacks. Specifically, this type of light has a relatively low intensity and brightness. The light from an incandescent bulb is also neither coherent nor collimated in a single direction. Therefore, the individual light particles, or photons, do not oscillate in phase with one another. Lasers do not have the above-mentioned drawbacks that result from light of an incandescent bulb. However, instead of emitting white light, a laser emits a narrow band of frequencies, resulting in light of a specific color. For many applications, coherent light at a single frequency, or a narrow band of frequencies, is more than adequate. However, having a light source, such as the SC, which combines the properties of a laser with those of a broad bandwidth incandescent bulb, provides for a new realm of applications.

Seminal work on the SC's generation was performed when it was discovered in 1970. See, R. R. Alfano et al., PRL, 24, 592-594, 584-587, 1219-1222, (1970). 100 Mega-Watt (MW), 10 picosecond (ps) pulses were focused into condensed materials in order to produce the SC with a white light continuum of colors. The SC light can be generated over a frequency octave using microstructure fibers, holey filters, and photonic crystal fibers, and using modest energies of <100 femtosecond (fs) ps lasers. See, K. J. Ranha et al., Opt. Lett. 25, 25 (2000), and S. Coen, Chau, Leonhardt, and J. Harvey, JOSA B, 26, 753 (2002). Using kilowatt peak power fs pulses, SC spans from 400 to 1600 nanometers (mu) can be generated in photonic crystal fibers. For example, 1 meter of NonLinear-Polarization Maintaining (NL-PM) 750 photonic crystal fiber made by Crystal Fibre Corp. can produce more than an octave, i.e., 1200 nm bandwidth using 800 nm 50 fs-67 milliWatt (mW) average power from a Ti-sapphire laser. The broad SC spectrum results from Self-Phase Modulation (SPM), 4 Wave Mixing (4WM), and stimulated Raman and Soliton generation. Thus, the SC light can be generated on a spectrum greater than an octave, where 500 to 1000 mu is an octave, and a two octave SC spans from 400 to 1600 nm.

A bright SC beam can be produced by focusing ~350 microJoule (μJ) 70 fs pulses from Ti-sapphire laser systems into a long metallic cylinder of 90 centimeters (cm), which contains rare gases, such as, for example, Argon (Ar), Krypton (Kr) and Xenon (Xe), at modest pressures from 2 to 30 Atmospheres (atm). See, P. B. Corkum et al., PRL, 57, 2268 (1986). The nonlinear parameter, $n_2$, for Ar is $9.8 \times 10^{-20}$ cm$^2$/W atm, for Kr is $2.8 \times 10^{-19}$ cm$^2$/W atm, and for Xe is $8.2 \times 10^{-20}$ cm$^2$/W atm. See, Lehmeier et al., Opt. Comm., 56, 67-72 (1985).

A milliJoule (mJ), which is the energy required to lift a paper clip several centimeters against the earth's gravity, may appear to be a small amount of energy. However, when a mJ is packed into a ps and focused into a tight spot it represents a GigaWatt (GW) of power and an extremely high intensity. With this high intensity, the pulses can propagate through a few centimeters (cm) of glass, inducing a Kerr effect strong enough to spread the pulses' bandwidth considerably even in the short time that they passed through the glass by distortion of the electron clouds in the material.

Fibers used for SC generation are known as microstructure fibers. A cross section of such fibers reveals a pattern of holes that runs continuously through the entire length of the fibers. In one commonly used design, the pattern of holes surrounds a solid silica core, similar to a honeycomb with only the central hole filled. The core has a high index of refraction, whereas the surrounding cladding, with its air holes interspersed with silica, has a lower refraction index. The concentric arrangement of refractive indices serves to guide the light pulses along the fiber. The use of these fibers with zero and anomalous dispersion, has enabled the generation of the SC light extending more than two octaves from InfraRed (IR) to UltraViolet (UV). The placement of the zero dispersion point in the fibers in blue and Near InfraRed (NIR) will produce pulses covering UV, visible, and NIR regions.

The generation of the SC light in optical fibers has unleashed a wide range of applications. One of the most important and mature of these applications is the development of extremely accurate frequency measurements and clocks. The SC light is useful in optical frequency comb techniques, which enable improved accuracy with simpler and smaller systems. Specifically, self-referencing becomes possible when the frequency comb extends across a full octave. In this approach, the frequency of light is doubled at the low-frequency end of the spectrum and is used to interfere with light at the high-frequency end.

Researchers are now striving to develop systems capable of measuring frequencies to a fractional accuracy of $10^{-16}$ to $10^{-18}$. Such extreme accuracy would have practical implications for improvements in Global Positioning Systems, space navigation, and the alignment of very large arrays of radio telescopes. The systems would also be utilized in tests of special relativity and related fundamental principles such as the isotropy of space, the symmetry of matter and antimatter, and the constancy of the constants of nature.

Frequency measurements and clocks are two facets of the same technology. Ultimately, the optical frequency comb might enable fractional accuracies of $10^{-18}$, which would be ideal for timing in optical computers and even for detecting oil and mineral deposits by their minute effects on the nearby gravitational field. The SC light is also enabling technology to produce shorter pulses into attosecond ($10^{-18}$ sec) and zeptosecond ($10^{-21}$ sec) regions.

An application with more immediate commercial implications than ultra-precise frequency measurements is telecommunications. Several of the SC's key properties make it an ideal basis for telecommunication systems that are capable of transmitting data more than 1,000 times faster than present-day systems. Optical fiber carrying IR light is already the most widely used means of sending data at high rates over long distances. In an effort to keep up with the ever-increasing worldwide demand for larger-capacity communications systems and networks, there is a need to include more data into a fiber. The goal is to achieve transmission rates of terabits ($10^{12}$) and pentabits ($10^{15}$) per second. Typical fiber-optic systems currently transmit data between cities at about 10 gigabits per second, or 0.01 terabit per second.

The ultrabroad bandwidth of the SC light makes it a cost-effective way to obtain numerous wavelength channels without having to use hundreds of lasers. That bandwidth could be utilized in superdense wavelength division multiplexing, in which data streams are encoded onto many different wavelengths of light that are transmitted simultaneously. The SC, unlike the light from 100 individual lasers, can be coherent across a wide range of frequencies, which aids in the degree of control that can be brought to bear on the light.

Alternatively, a series of ultrashort pulses of the SC light (shorter than 100 fs, or $10^{-13}$ second) can be sent, with sequences representing different data channels interleaved with one another, referred to as Time-Division Multiplexing (TDM). With short pulses, it is important to be able to control the precise relation between the individual oscillations of the electric field (the carrier wave) and the pulse envelope. This property, referred to as the relative phase of the carrier and the envelope, determines, for example, whether the peak of the pulse envelope occurs at an instant when the electric field of the wave is at a peak or a trough, or somewhere in between. The properties of the SC light facilitate such control.

Data transmission rates of terabits/second have already been achieved using a small segment of the SC light spectrum. However, many challenges remain in order to improve the speed and achieve petabit/second operation. These challenges include reducing the duration of a bit to about a ps and increasing the number of coherent wavelengths in the SC.

The telecommunication applications rely on producing the SC light in the completely controlled environment of an optical fiber; however, for some applications the SC light is generated in open air. One such application is the remote sensing of molecular species present in air. When intense ultrafast laser pulses travel through the air, they can produce long, narrow "filaments" in which the air is ionized. Within those filaments electrons are knocked off the air's molecules, forming a plasma of positive ions and negatively charged electrons. These filaments can guide the light pulses and keep them from spreading, a process that scientists attribute to a balance between defocusing caused by diffraction (the tendency for a wave to spread out from a small aperture) and self-focusing caused by the ionized plasma.

Within the filaments a significant amount of the pulses' power can convert to SC white light over distances greater than 20 meters. Pollutants and aerosols in the air will absorb the light at characteristic frequencies, and the broad spectrum of the SC light enables one to detect their absorption spectra simultaneously in the UV, visible and IR bands.

In addition to probing the air around us, the SC light is useful in producing high-resolution images of tissues within us. Optical Coherence Tomography (OCT), can be carried out in situ in living organisms as a diagnostic tool to measure tissue layers.

To produce an OCT image, a light is split into two parts. A first part of the light illuminates a spot in the sample, whereas a second part, or a reference light, enters a length of fiber. When the reference light recombines with light that the sample reflected or scattered, the two interfere strongly, provided that they each spent the same length of time on their respective journeys. High-resolution OCT imaging relies on a short coherence length of the source light, which requires a very accurate timing match.

Thus, when the spot of light penetrates into the sample, only light coming back from one specific depth will interfere with the reference light. Scanning the light laterally across the sample while keeping the travel time of the reference light fixed thereby produces a two-dimensional image of the sample at a certain depth. The thickness of the layer that contributes to the image is called the axial resolution of the image.

Early OCT imaging systems relied on a type of diode to provide the light and had an axial resolution of 10 to 15 microns. The axial resolution also depends on the bandwidth of the light source. A broader bandwidth enables finer resolution. The SC light has a short coherence length and a bandwidth broader than any fs laser, making it ideal for high-resolution OCT imaging. The SC light generated in microstructured fibers has been used to produce images of cells with an axial resolution of 0.5 micron.

Light is also capable of photo-activating molecular components within tissue (in the matrix and/or cells) in order to fuse a cut together with minimal scarring using the water absorption from overtone and combination vibrational bonds at 1450 nm, spanning from 1000 to 1600 nm. Tissue welding can be achieved using lasers, such as tunable $Cr^{4+}$ lasers, semiconductor lasers, and fiber lasers, where the weld strength follows the absorption spectrum of water. Tissue wounds, bruises, and burns can be healed using laser and lamp light covering UV to visible regions at an average irradiance of ~100 $mW/cm^2$. Microsecond pulsed lasers from 1850 nm to 2100 nm may be used to stimulate nerves, and to kill bacteria and viruses by exciting upper UV states with UV and blue light transitions.

SUMMARY OF THE INVENTION

The present invention has been made to address at least the above problems and/or disadvantages and to provide at least the advantages described below. Accordingly, an aspect of the present invention provides a method and an apparatus for providing the SC light for medical and biological applications According to one aspect of the present invention, an apparatus is provided for producing SC light for medical and biological applications. The apparatus includes a laser system for producing pulses. The apparatus also includes at least one of a pressurized cell and one or more fibers for receiving the pulses for conversion into the SC light at a specified rate of repetition and application of the SC light at the specified rate of repetition to a tissue for medical and biological applications. The pulses are focused through a lens having a focal length of approximately 100-200 centimeters (cm) for the pressurized cell, and the pulses are focused through a microscope objective lens having 10×-40× magnification for the one or more fibers.

According to another aspect of the present invention, a method is provided for producing SC light for medical and biological applications. Pulses are produced from a laser system. The pulses are focused with at least one of a lens having a focal length of approximately 100 to 200 centimeters (cm) and a microscope objective lens having 10×-40× magnification. The lens focuses the pulses into a pressurized cell and the microscope objective lens focuses the pulses into one or more fibers. The pulse is converted into the SC light at a specified rate of repetition. The SC light is applied at the specified rate of repetition to tissue for medical and biological applications.

BRIEF DESCRIPTION OF THE DRAWINGS

The above and other aspects, features and advantages of the present invention will be more apparent from the following description when taken in conjunction with the accompanying drawings, in which.

DETAILED DESCRIPTION OF EMBODIMENTS OF THE PRESENT INVENTION

Embodiments of the present invention are described in detail with reference to the accompanying drawings. The same or similar components may be designated by the same or similar reference numerals although they are illustrated in different drawings. Detailed descriptions of constructions or processes known in the art may be omitted to avoid obscuring the subject matter of the present invention.

The terms and words used in the following description and claims are not limited to their dictionary meanings, but are merely used to enable a clear and consistent understanding of the invention. Accordingly, it should be apparent to those skilled in the art that the following description of embodiments of the present invention are provided for illustrative purposes only and not for the purpose of limiting the invention, as defined by the appended claims and their equivalents.

It is to be understood that the singular forms "a," "an," and "the" include plural referents unless the context clearly dictates otherwise. Thus, for example, reference to "an identifier" includes reference to one or more of such identifiers.

The embodiments of the present invention relate to medical and biological applications using the SC. The SC light is incorporated into the field of medicine, specifically, for use in therapeutic biomedical applications in humans and animals, on the skin or within the body using optical fibers. Such applications may include the healing of wounds and bruises, the bonding of cut tissues, and the killing of bacteria and viruses through the generation of nonlinear effects. The SC light consists of ultrashort pulses spanning an ultrabroad spectral region at a high rate of repetition. The SC light spans the UV-visible-NIR spectrum with the ultrashort pulse duration being <10 ps, and typically <100 fs.

The brightness of the SC light surpasses that of the sun hitting the surface of the earth, as well as other lasers over such a broad spectral coverage. The spectrum of the SC light is so wide that it can excite most molecules in tissue via single and multiple photon absorption from electronic transitions and combination and overtone vibrational transitions. The non-thermal excited state directly causes new interactions, chemical reactions, optical catalysts, enzyme actions and the formation of new bondings.

The SC light stimulates molecular activity of the native molecules in the tissue by exciting their electronic states and overtone and combination vibrational states via absorption. It is well known that excited energy states of molecules are the most active. For example, the energy state of oxygen, which is normally in triplet state $^3O_2$, can be excited to a singlet state $^1O_2$ in order to oxidize surrounding molecules. The key molecules and bonds in tissue that can be excited by the SC light include collagen, elastin, tryptophan, water, proteins, NAPHs, genes, porphyrins, peptides, flavins, amino acids, blood, hemoglobin, and amide I, II, III, A.

On a molecular level, the distribution of excited molecules among higher energy states will appear to be "hot" at temperature $T_0$, since the higher energy states are far beyond the normal populations. The photoexcited molecules behave as if the system was heated to an extreme temperature ($T_0$) during the pumping time of <10 ps. However, the host containing the non-excited molecules will actually be at room temperature $T_{RT}$. The chemical reactions will proceed at a much faster rate at the "hot" temperature, $T_0$, overcoming any potential barriers in reaction coordinate space and acting like an optical catalyst. There is no damage to the host since the tissue is not actually "hot."

For example, photoexcited "hot" ($T_0$) molecules of water and collagen will cause rebonding of the hydrogen bonds and collagen-collagen-$H_2O$-bonds, where the collagen rewinds via $H_2O$ coupling and matches up the ends of chains. Additionally, new collagen will form by photo stimulation.

Figure 1:
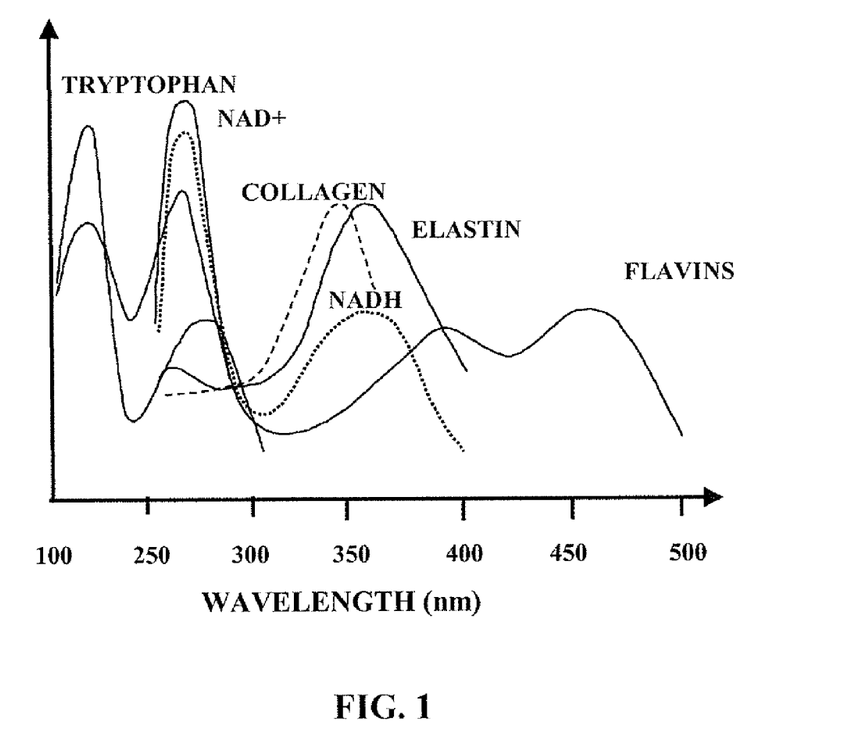
FIG. 1 is graph illustrating absorption spectral bands of electronic states of key molecules in cells and tissue structure, according to an embodiment of the present invention.

The entire ultra-broad spectrum of the SC, or a selected portion using optical filters, can be used to selectively excite a particular molecular group or bonds. In tissue, there are many key native molecules with absorptions from electronic transitions $S_0 \rightarrow S_1$, $S_2$ covering a 280-500 nm band. The absorption spectral bands of electronic states of key molecules in cells and tissue structure are shown in FIG. 1. These molecules include, for example, collagen at ~340 nm, elastin at ~380 nm, flavins at ~300 nm, tryptophan at ~280 nm, proteins at 280-400 nm, DNA at 230-280 nm, and RNA at 240-280 nm.

Figure 2:
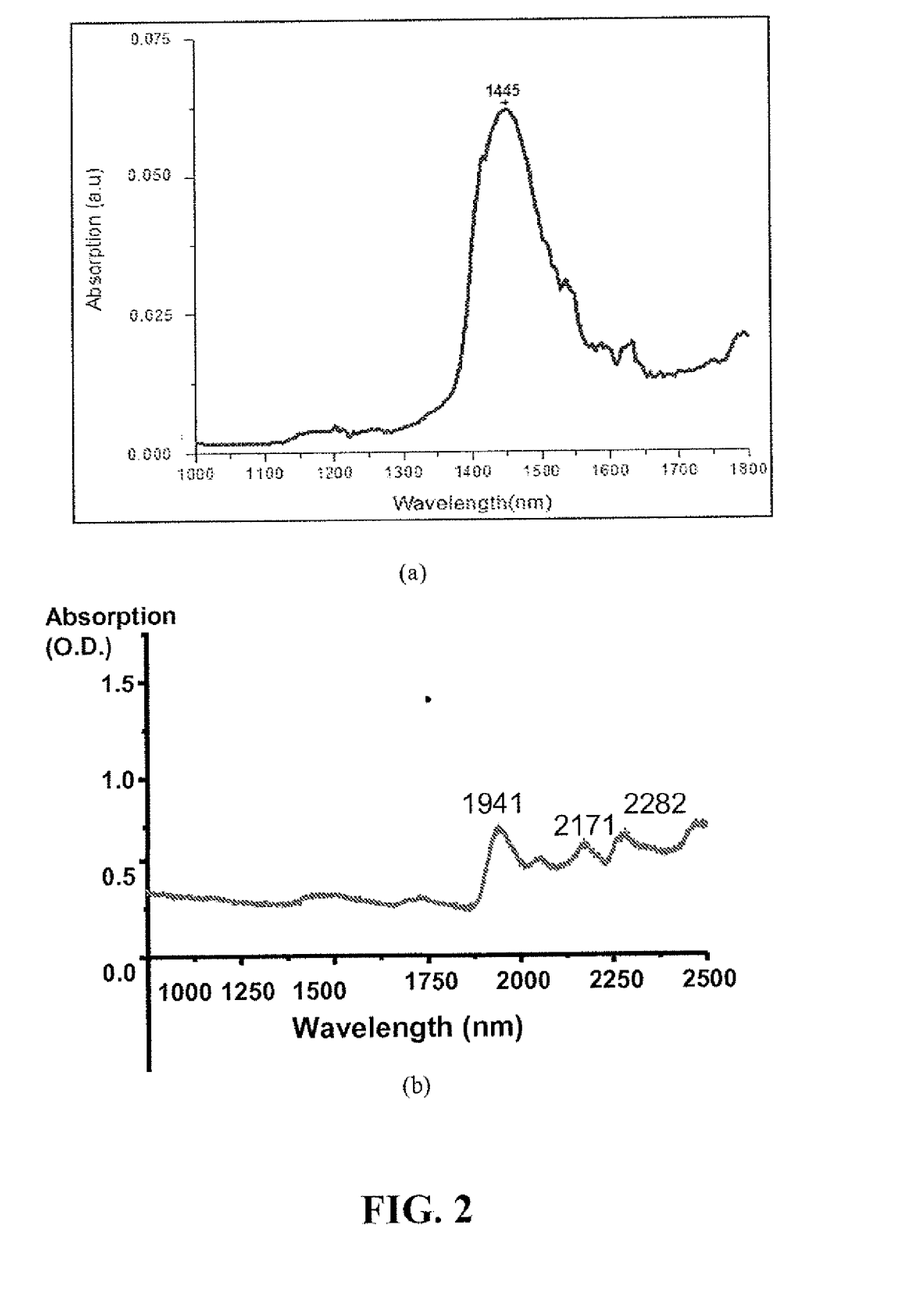
FIGS. 2(a) AND 2(b) are graphs illustrating overtone and combination vibrational absorption bonds of water and collagen in tissue, according to an embodiment of the present invention.

There are also key native molecules with absorptions from overtone and combination vibrational modes covering the NIR band from 800-2500 nm. These molecules include water at 900-1600 and 1900 nm, collagen at 1600-2500 nm, and elastin at 1700-2400 nm. The overtone and combination vibrational absorption bonds of water and collagen in tissue are shown in FIG. 2. The absorption peaks of collagen are, for example, at 1750 nm, 1950 nm, 2250, while those for elastin are, for example, at 1600 mu, 1750 nm, 2150 nm, 2200 nm, and 2300 nm.

Figure 3:
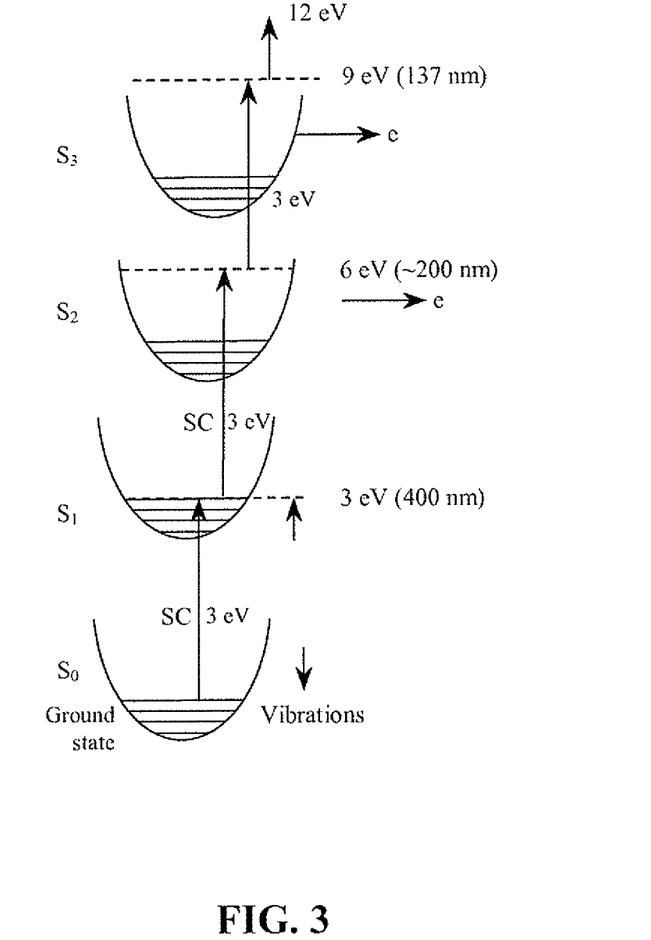
FIG. 3 is a diagram illustrating multiple photo transitions of polyatomic molecules to reach upper electronic states, according to an embodiment of the present invention.

FIG. 3 shows multiple photon transitions of polyatomic molecules to reach upper electronic states for the ionization and destruction of bacteria, viruses, and cancers. The SC light can have a spectral irradiance of GW/nm cm$^2$ from a selected spectral portion to create nonlinear optical effects in materials to enter into an extreme UV region and excite molecules in upper electronic states, $S_n$ (n=2, 3, 4, . . . ). This disassociates polyatomic bonds and causes an avalanche breakdown in organic molecules to kill bacteria, viruses, and cancers as shown in Equation (1) below:

(1)

The ground state $S_0$ absorbs photons from photon energy by of SC followed by ionization and disassociation generating avalanche electrons e to break bonds as shown in FIG. 3.

Figure 4:
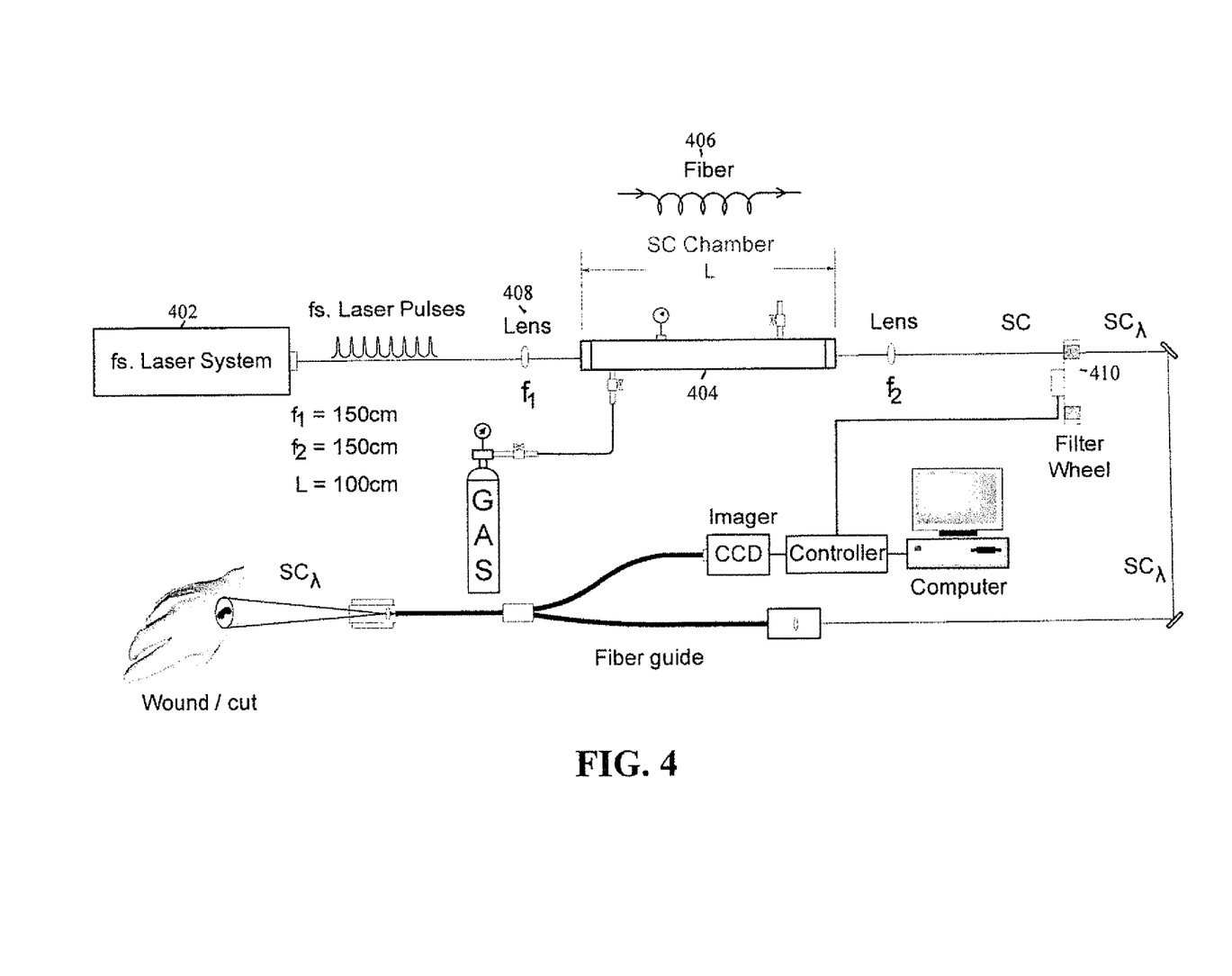
FIG. 4 is a diagram illustrating an SC generation setup for medical and biological applications, according to an embodiment of the present invention.

FIG. 4 is a diagram illustrating an example of a setup for medical and biological applications for using the SC light from a fiber or gas cell, according to an embodiment of the present invention. In accordance with an embodiment of the present invention, <100 fs pulses from a laser system 402 are focused into a pressurized cell 404 containing a rare gas, or a fiber 406, to convert an entire pump pulse of ~1 mJ into the SC light at a repetition rate of ~1 kiloHertz (kHz). The laser system may be a Ti-sapphire and Second Harmonic Generation (SHG) laser system with ~400 nm and ~800 nm pulses. The laser system may also be a Cr:Forsterite laser system with ~1250 mm pulses. The laser system may further be a LiInGeO4 (LIGO) or LiInSiO4 (LISO) laser system with ~1500 nm pulses. The pressurized cell 404 has a length ranging from 100-150 cm, and preferably ~100 cm. The pressurized cell 404 contains ~2-10 atoms of a rare gas, such as (Ar), (Kr) or (Xe).

The pulses are focused through a long focus lens 408, having a focal length between approximately 100-200 cm, and preferably ~150 cm, for introduction into pressurized cell 404. Alternatively, the pulses may be focused through a microscope objective lens at approximately 10×-40× magnification for introduction to the fiber 406. The pulses proceed through an exiting lens to an optical filter wheel 410 with narrow band filters that are approximately 5-100 nm in width. A resulting center frequency, which covers UV, visible and NIR regions, is then delivered to wound for healing effects.

For an SC span of about 1000 nm, a peak spectral energy is defined as shown in Equation (2) below:

$$\frac{1 \, mJ}{1000 \, nm} \quad (2)$$

This value will give the peak spectral energy as defined as shown in Equation (3) below:

$$\varepsilon_\lambda = \frac{1 \, \mu J}{nm}. \quad (3)$$

A peak spectral energy flux (irradiance-energy per area) of the SC light for a beam size of 1 nm is defined as shown in Equation (4) below:

$$\frac{\varepsilon_\lambda}{A} = \frac{100 \, \mu J}{nmcm^2} \quad (4)$$

For a 100 fs pulse, a peak spectral power intensity is defined as shown in Equation (5) below:

$$\frac{P_\lambda}{A} = \frac{10^9 \, watt}{nmcm^2} = \frac{GW}{nmcm^2}. \quad (5)$$

This peak spectral power flux is sufficient to produce a variety of nonlinear optical effects via $\chi_2$ and $\chi_3$ processes such as SHG, Stimulated Raman Scattering (SRS), 4WM, Third Harmonic Generation (THG) and self-focusing at different spectral wavelength bands of 1 nm to 10 nm at 1 GW/cm² to 10 GW/cm².

Focusing this SC beam into 100 μm spot size results in a peak spectral power flux at the focal spot as defined in Equation (6) below:

$$\frac{P_\lambda}{A} = \frac{10^{11} \, watt}{nm} = 0.1 \frac{Terawatt}{nm} \quad (6)$$

There is enough power to ionize most materials and create nonlinear optical effects with a spectral selected window of a few nanometers. This power level of the SC light in blue can produce two, three and higher photon absorption transitions in tissue, bacteria and viruses, such that these elements and even cancers may be destroyed.

From Equation (4) above, the average spectral brightness (average spectral irradiance $$\left(\frac{power}{area}\right)$$

of SC for a 1 kHz rate pulse train is defined as shown in Equation (7) below:

$$\frac{\overline{P}_\lambda}{A} = \frac{100 \, \mu j}{cm^2 nm} \times (10^3 Hz) = 100 \frac{milliwatts}{nmcm^2} \quad (7)$$

The brightness of the SC light over the entire bandwidth of ~1000 nm is defined as shown in Equation (8) below:

$$\frac{\overline{P}}{A} = \frac{100 \, watts}{cm^2} \quad (8)$$

The brightness of the sun hitting the surface of the earth at 1370 watt/m² is defined as shown in Equation (9) below:

$$\frac{\overline{P}}{A} = 0.137 \frac{watt}{cm^2} \quad (9)$$

The solid angle Ω of the sun is 7×10⁻⁵ radii and SC is ~4×10⁻⁶ radii. The full SC white light brightness is more than the sun hitting the earth. Typical irradiance needed for healing is ~10 mW/cm²-100 mW/cm² in visible and NIR using selected wavelengths. The SC light has this irradiance.

The brightness of the sun or an intensity of a 1000 Watt/m² DC lamp has ~0.1 W/cm², which gives an energy within 10⁻¹³ sec over an area of 1 cm², is defined in Equation (10) below:

$$E = 10^{-14} J \quad (10)$$

The energy of SC over 1 cm² in a one nanometer band is 100 µJ, i.e. $10^{-4}$ J. The ratio of energies between SC and E is defined in Equation (11) below:

$$E_{SC}/E = 10^{-4}/10^{-14} = 10^{10} \tag{11}$$

The energy of SC is much larger than Continuous Wave (CW) by over $10^{10}$ for 100 fs.

The number of photons in SC at the wavelength of 500 nm is defined in Equation (12) below.

$$N_{SC500} = 2.5 \times 10^{14} \text{ photons}, \tag{12}$$

The number of photons in the light of the sun within $10^{-13}$ sec time span is defined in Equation (13) below:

$$N_{sun} = 2.5 \times 10^4 \text{ photons} \tag{13}$$

The ratio of Equation (14) can induce nonthermal reactions and changes in materials to heal.

$$N_{SC500}/N_{sun} = 10^{10}, \tag{14}$$

Referring again to FIG. 4, a microstructure or photonic crystal fiber 406 can be utilized in place of the pressurized cell 404. Small core microstructure fibers with an air filling factor (f) can cover UV, visible, and NIR regions using Self Phase Modulation (SPM), Cross Phase Modulation (XPM), 4WM, and soliton at pump wavelengths near zero dispersion fibers in the visible and NIR regions. For example, a 1 µm core quartz fiber has two zero group velocity dispersion points at both 550 nm and 1200 nm wavelengths for f=1, and a 1.7 µm core fiber has two zero dispersion points at 750 nm and 1500 nm with a full factor of f=0.5. These fibers will produce the SC light from blue to NIR.

About a 600 nm diameter core fiber has two zero dispersion wavelengths at 350 nm and 1200 nm. This fiber is ideal for SC generation and covers the spectral band from 300 nm to 1400 nm spanning UV to NIR. The 1 µm core fiber covers the SC light spectrum from 400 to 1400 nm using both SPM and XPM.

Thus, as shown in FIG. 4, the SC light can be used for therapeutic applications of healing wounds, healing bruises, healing burns, fusing cut tissue, and welding tissues by exciting electronic and vibrational states of the underlying molecules in tissue and skin. Tissues may be healed with less scarring, and arteries may be healed and fused with reduced scarring. The SC light can produce angiogenesis for an increase in new blood vessels, blood flow and improved healing. A small room may also be flooded with the SC light to heal tissue damage and wounds of patients.

As described above, upper electronic state excitation by multi photon absorption (2, 3, and 4 photons from the SC) can lead to the rupturing of bonds and ionization of polyatomic molecules, such as bacteria, viruses, and cancers.

Nerve stimulation using electric pulses is used for therapeutic treatment of Parkinson, Alzheimer, and other brain and nerve diseases. Electrical stimulation of nerves requires contacts with metal electrodes inserted into tissue to make contact precisely near nerves in skin. Optical stimulation can deliver the signal deep into the tissue allowing more selective excitation. IR laser pulse radiation at 1600 to 2300 nm is suitable to stimulate nerves. The SC light offers greater potential to stimulate neural activity using a portion of a signal spectra from 800 nm to 1700 nm to excite the vibrations of water and lipids in the tissue to transfer energy from water and lipids through overtone and combination vibrations to axons and myelin complexes within the nerve.

Additional uses for the SC light in medical and biological applications include its use as a lamp in a projector during surgery to differentiate anatomical structures in selected colors. Specifically, deoxygenation and oxygenation regions and cancerous and non-cancerous regions may be differentiated, via scattering and emission from the key molecules in tissues described above.

While the invention has been shown and described with reference to certain embodiments thereof, it will be understood by those skilled in the art that various changes in form and detail may be made therein without departing from the spirit and scope of the invention as defined by the appended claims and their equivalents.

What is claimed is:

1. A method of photo-activating molecular components within a matrix and/or cells of biological tissue to be treated for a specified medical condition, comprising the steps of exposing the tissue to pulses of supercontinuum (SC) light that has a spectral irradiance equal to at least 1 GW/nm cm² that creates nonlinear optical effects in materials that excites molecules into upper electronic states and disassociates polyatomic bonds causing a breakdown in organic molecules for at least one of the following medical and biological applications: healing wounds, burns, cuts and bruises, fusing arteries, reducing scarring, producing angiogenesis, stimulating nerves, and killing bacteria, viruses and cancer cells; selecting at least one predetermined band of the supercontinuum light to excite electronic states of native molecules and/or overtone and combinational vibrational states of the native molecules associated with specified medical condition; and adjusting the rate of said pulses and duration of exposure to treat the specified medical condition using one, two and three photon absorption using selected zones in SC light.

2. A method as defined in claim 1, wherein said pulses are provided at about <100 femtoseconds (fs) to <10 ps.

3. A method as defined in claim 1, wherein said pulses are adjusted to have a repetition rate of approximately 1 kilohertz (kH) up to 100 Megahetz for different modelock operation of Ti sapphire laser.

4. A method as defined in claim 1, wherein the supercontinuum light is used to stimulate molecular activity of native molecules in the tissue by exciting electronic states and overtone and combination vibrational states of the native molecules via absorption using one and multi photon absorption.

5. A method as defined in claim 4, wherein a 280-500 nm band of the SC light is used to excite the electronic states of the native molecules, and an 800-2500 nm band is used to excite overtone and combination vibrational states of the native molecules.

6. A method as defined in claim 5, wherein the native molecules having excited electronic states comprise one or more of collagen, elastin, flavins, tryptophan, proteins, DNA, RNA and amino acids.

7. A method as defined in claim 5, wherein the native molecules having excited overtone and combination vibrational states comprise one or more of water, collagen and elastin.

8. A method as defined in claim 7, wherein absorption peaks of collagen are at one or more of 1750 nm, 1950 nm and 2250 nm, and absorption peaks for elastin are at one or more of 1600 nm, 1750 nm, 2150 nm, 2200 nm and 2300 nm.

9. A method as defined in claim 1, wherein the nonlinear optical effects comprise SHG, Stimulated Raman Scattering (SRS), 4 Wave Mixing (4WM), Third Harmonic Generation (THG) and self focusing.

10. A method as defined in claim 1, wherein a spectrum of the SC light covering UltraViolet (UV), visible and Near InfraRed (NIR) bands is created through at least one of Self Phase Modulation (SPM), Cross Phase Modulation (XPM) and 4WM use one, two or three photon absorption.

11. A method as defined in claim 1, wherein an 800-1700 nm band of the SC light stimulates nerves to be activated via vibrational excitation of water and lipid molecules near the nerves for therapeutic improvement of nerve based diseases.

12. A method of photo-activating molecular components within a matrix and/or cells of biological tissue to be fused or welded at a point where the tissue is cut, comprising the steps of exposing the tissue to pulses of supercontinuum (SC) light that has a spectral irradiance equal to at least 1 GW/nm cm$^2$ that creates nonlinear optical effects in materials that excites molecules into upper electronic states and disassociates polyatomic bonds causing a breakdown in organic molecules for at least one of the following medical and biological applications: healing wounds, burns, cuts and bruises, fusing arteries, reducing scarring, producing angiogenesis, stimulating nerves, and killing bacteria, viruses and cancer cells; selecting a band of light spanning the supercontinuum from approximately 280 nm-2500 nm to induce water absorption by exciting electronic states and/or overtone and combinational vibrational states of the native molecules surrounding the cut tissue; and adjusting the rate of said pulses and duration of exposure to fuse a cut together with minimal scarring.

13. A method as defined in claim 12, wherein the band of light is centered at about 1445 nm.

14. A method as defined in claim 12, wherein said supercontinuum and UV light to visible regions are used to heal tissue wounds, bruises and burns.

15. A method as defined in claim 14, wherein the tissue is irradiated at a level of approximately 10 mW/cm$^2$ of 100 mW/cm$^2$.

16. A method as defined in claim 12, wherein the tissue is nerve used tissue and the supercontinuum light is used to stimulate neural activity.

17. A method as defined in claim 12, wherein the tissue is blood vessel tissue and the supercontinuum is used to heal and/or fuse the tissue and/or promote angiogenesis to enhance growth of blood vessels and flow of blood.

18. A method of photo-activating molecular components within a matrix and/or cells of biological substances comprising the steps of exposing the biological substances to pulses of supercontinuum (SC) light that has a spectral irradiance equal to at least 1 GW/nm cm$^2$ that creates nonlinear optical effects in materials that excites molecules into upper electronic states and disassociates polyatomic bonds causing a breakdown in organic molecules for at least one of the following medical and biological applications: healing wounds, burns, cuts and bruises, fusing arteries, reducing scarring, producing angiogenesis, stimulating nerves, and killing bacteria, viruses and cancer cells; selecting at least one predetermined band of supercontinuum light to excite electronic states of native molecules and/or overtone and combinational vibrational states of the native molecules associated with the biological substances by multi-photon absorption; and adjusting the rate of said pulses and duration of exposure to rupture the bonds of the biological substances and ionize polyatomic molecules to neutralize the biological substances.

19. A method as defined in claim 1, wherein exposing comprises imaging one of brain, prostate, breast by linear and nonlinear (2 or 3 photon absorption) using the optical windows of tissue and water like media, in the wavelength windows or zones of less scattering to enhance imaging deep into tissue such as: 650 nm to 900 nm; 1150 nm to 1300 nm, 1600 nm to 1800 nm and 2100 to 2300 nm using an InGaAs and InSb CMOS or CCD cameras.

20. A method as defined in claim 1, wherein exposing comprises optical stimulation by using SC beams for applications on brain and nerve tissues for Alzheimer's, Parkinson, nerves in skin (shingles).

21. A method as defined in claim 1, wherein SC light is used for tissue welding of tissue wounds, bruises, and burns wherein welding strength follows the absorption spectrum of water from 1400 nm to 1600 nm and Collagen at 1600 nm to 1800 nm using an average irradiance of ~100 mW/cm2.

22. A method as defined in claim 1, wherein SC pulsed lasers from 1850 nm to 2100 nm are used to stimulate nerves.

23. A method as defined in claim 1, wherein SC pulsed lasers are used to kill bacteria and viruses by exciting upper UV states with UV and blue light transitions.

24. A method as defined in claim 1, wherein SC light is used to provide SC IR laser pulse radiation at 1600 to 2300 nm for stimulation signal deep into the tissue up to mm allowing more selective excitation suitable for treating Parkinson Alzheimer, Shingles and other brain and nerve disorders from optical stimulation of nerves.

25. A method as defined in claim 1, wherein the SC light is used to stimulate neural activity using a portion of a signal spectra from 800 nm to 2300 nm to excite the vibrations of water and lipids in the tissue to transfer energy from water and lipids through overtone and combination vibrations to axons, neurons, and myelin complexes within the nerve and brain.

* * * * *